US011226276B2

(12) United States Patent
Fuchs et al.

(10) Patent No.: US 11,226,276 B2
(45) Date of Patent: Jan. 18, 2022

(54) SENSOR APPARATUS FOR METAL PARTICLES IN FLUIDS

(71) Applicant: HYDAC ELECTRONIC GMBH, Saarbruecken (DE)

(72) Inventors: Patrik Fuchs, Kirkel (DE); Heinz Jacobus, Dudweiler (DE)

(73) Assignee: HYDAC ELECTRONIC GMBH, Saarbruecken (DE)

( * ) Notice: Subject to any disclaimer, the term of this patent is extended or adjusted under 35 U.S.C. 154(b) by 0 days.

(21) Appl. No.: 16/959,467

(22) PCT Filed: Dec. 21, 2018

(86) PCT No.: PCT/EP2018/086569
§ 371 (c)(1),
(2) Date: Jul. 23, 2020

(87) PCT Pub. No.: WO2019/134857
PCT Pub. Date: Jul. 11, 2019

(65) Prior Publication Data
US 2021/0072136 A1 Mar. 11, 2021

(30) Foreign Application Priority Data
Jan. 8, 2018 (DE) .................... 10 2018 000 079.7

(51) Int. Cl.
*G01N 15/06* (2006.01)
(52) U.S. Cl.
CPC ................ *G01N 15/0656* (2013.01)
(58) Field of Classification Search
CPC ............ G01N 15/0656; G01N 33/2858; B03C 1/282; F16H 48/28; F16H 57/02; F16H 2057/126; F16H 2057/127
See application file for complete search history.

(56) References Cited

U.S. PATENT DOCUMENTS 3,263,698 A * 8/1966 Siggelin .............. F16K 17/0413
137/467
4,721,283 A * 1/1988 Wilson ................ F16K 31/1221
251/144
(Continued)

FOREIGN PATENT DOCUMENTS

CH 711 982 6/2017
DE 698 10 288 11/2003
(Continued)

OTHER PUBLICATIONS

International Search Report (ISR) dated Apr. 24, 2019 in International (PCT) No. PCT/EP2018/086569.

*Primary Examiner* — John Fitzgerald
*Assistant Examiner* — Truong D Phan
(74) *Attorney, Agent, or Firm* — Wenderoth, Lind & Ponack, L.L.P.

(57) ABSTRACT

A device has a sensor (1) for detecting a contamination in the form of metal particles in a fluid, and is at least partially encompassed by a partition wall (17). Partition wall (17) is at least partially penetrated via a receiving opening (55) by the sensor device (1) arranged in its functional position and comprising its sensor (25) detecting the metal particles. The sensor (1) can be removed from the partition wall (17) into an inoperative functional position, in particular for maintenance or replacement purposes. The sensor (1) interacts with a closing device (3) such that upon removal of the sensor (1) to its inoperative functional position, the closing device (3) closes the receiving opening (55). In the opposite direction, when the sensor (1) is brought into its functional position, this receiving opening (55) is released.

10 Claims, 3 Drawing Sheets

(56) References Cited

U.S. PATENT DOCUMENTS

| | | | | |
|---|---|---|---|---|
| 5,782,141 A | * | 7/1998 | Schoolcraft | B03C 1/282 74/606 R |
| 2011/0308619 A1 | * | 12/2011 | Martino | F16K 3/0254 137/1 |

FOREIGN PATENT DOCUMENTS

| | | | | |
|---|---|---|---|---|
| DE | 203 20 334 | | 5/2004 | |
| DE | 20320334 U1 | * | 5/2004 | G01N 27/283 |
| DE | 10 2011 121 528 | | 6/2013 | |
| EP | 0 893 683 | | 1/1999 | |
| EP | 0937925 A1 | * | 8/1999 | F16K 41/026 |
| JP | 2010-14518 | | 1/2010 | |

* cited by examiner

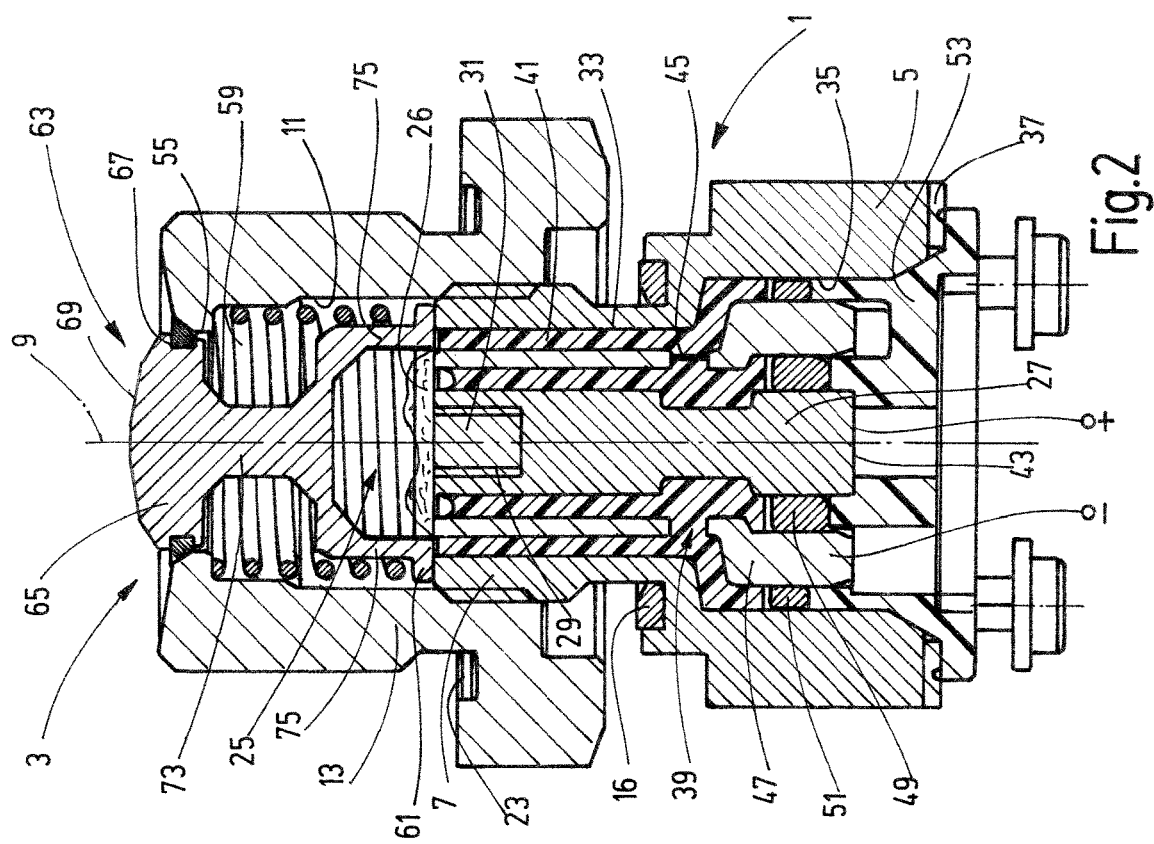
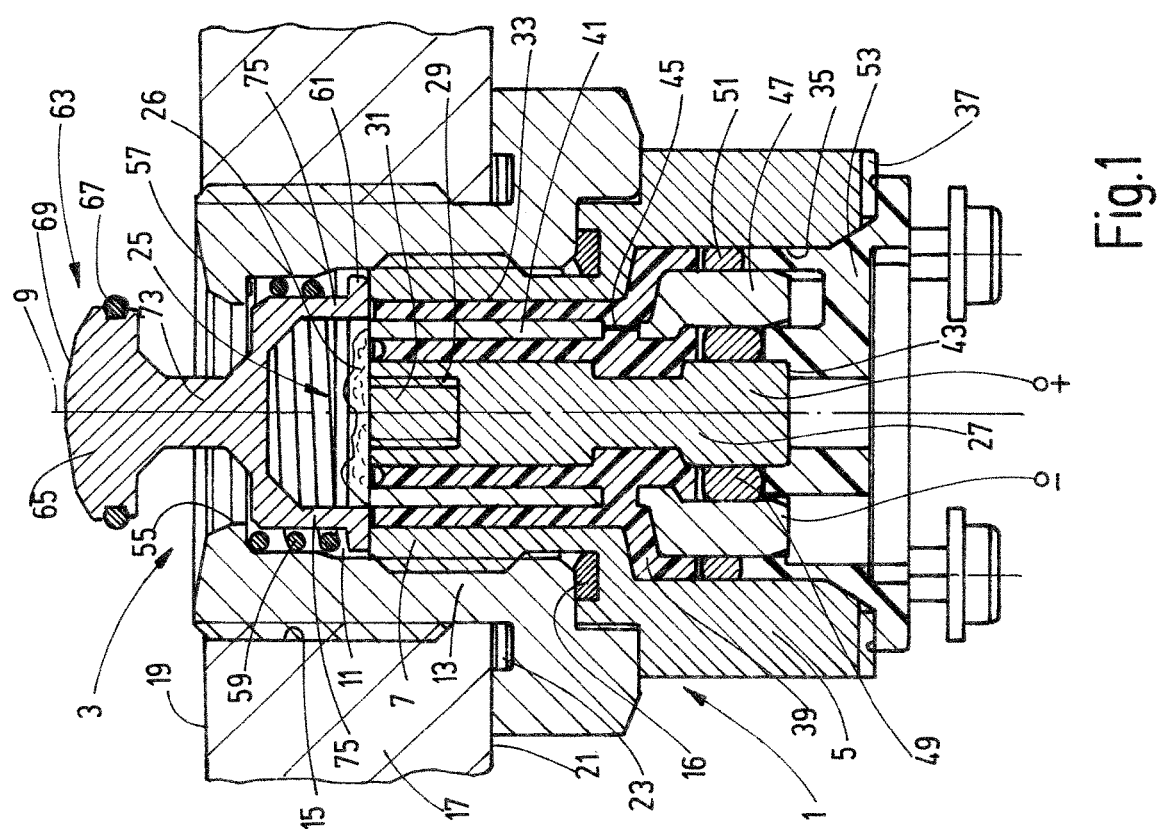

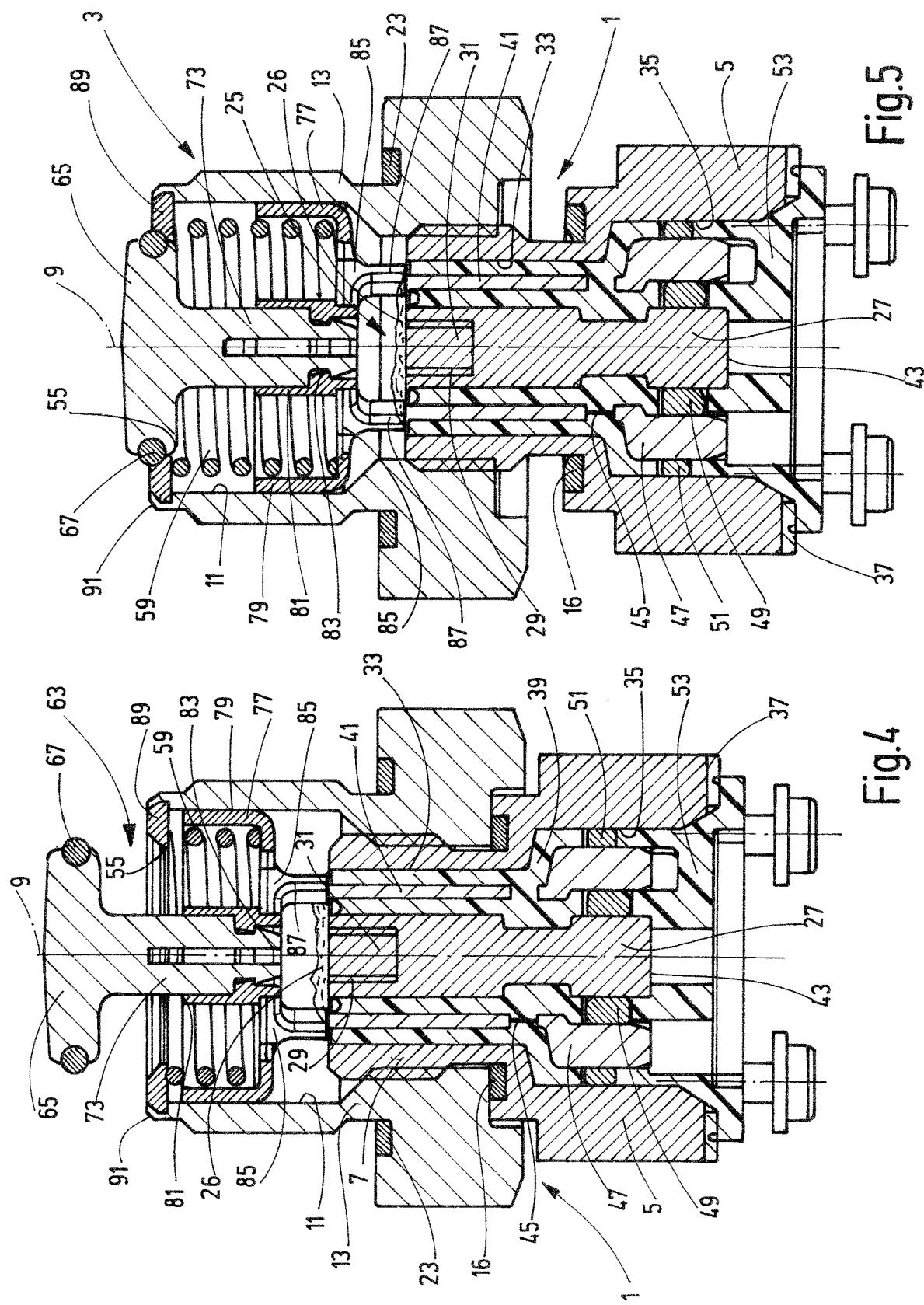

SENSOR APPARATUS FOR METAL PARTICLES IN FLUIDS

FIELD OF THE INVENTION

The invention relates to a device having a sensor device for detecting a contamination in the form of metal particles in a fluid. The sensor device is at least partially encompassed by a partition wall, which is at least partially penetrated via a receiving opening by the sensor device arranged in its functional position, and comprises its sensor detecting the metal particles. The sensor device can be removed from the partition wall into an inoperative functional position, in particular for maintenance or replacement purposes.

BACKGROUND OF THE INVENTION

Sensor devices of this type are state of the art, see EP 0 893 683 B1. Sensor devices of this type are used in particular in fluid systems, in which fluids, such as hydraulic oils or lubricating oils, flow through assigned system components, e.g. hydraulic pumps and hydraulic motors or gearboxes. These system components are subject to wear, contaminating the fluid with metal particles. These particles can settle in valves, in bearings lubricated by the fluid or in other components and cause damage there. The known sensor devices permit the detection of the contamination or a degree of contamination of the fluids with metal particles by determining the electrical resistance between two adjacent electrodes. The electrical resistance is dependent on the presence of metal particles between the electrodes.

In the state of the art, as with the solution described in EP 0 893 683 B1, a magnetic field is provided to collect ferromagnetic particles on the sensor device. An electrical signal generated on the basis of the determined resistance can be used to switch off the fluid system as soon as the degree of contamination has exceeded a predetermined threshold value, or to generate an alarm signal.

For reasons inherent in the system, such sensor devices require maintenance. In particular, after an aggregation of metal particles between the electrodes of the sensor, a cleaning process or a replacement has to be performed, for which the sensor device has to be removed from the wall separating the fluid area from the sensor, e.g. from a pipe wall, container wall or gearbox housing wall. Because it is normally impractical to empty the fluid area for the respective maintenance process, removing the sensor device from the partition wall is extremely problematic and may pose an environmental hazard because of fluid leakage.

SUMMARY OF THE INVENTION

With regard to this problem, the invention addresses the object of providing a sensor device of the type mentioned above, which is characterized by an improved operational behavior.

According to the invention, this object is basically solved by a sensor device having a sensor detector that interacts with a closing device such that upon removal of the sensor detector to its inoperative functional position, the closing device closes the receiving opening. In the opposite direction, when the sensor detector is brought into its functional position, the closing device releases this receiving opening. Because the process of removing the sensor detector from the partition wall in this way results in the closure of the receiving opening by the closing device, and thus, eliminates the problem of fluid leakage, maintenance or replacement work is simple and safe without any risk of environmental pollution.

In a particularly advantageous manner, the closing device can have a spring-loaded closing plate forming a kind of check valve. The closing plate can be brought into an open position releasing the receiving opening under the action of the sensor device against the action of its closing spring or into its blocking position blocking the receiving opening under the action of the closing spring. In this way, a closing device, which closes automatically when the sensor device is removed, can be implemented in a particularly simple construction.

In particularly advantageous embodiments, the receiving opening in the partition wall is delimited by a receiving housing, which can be inserted, in particular screwed, in the partition wall. The receiving housing permanently accommodates the closing device and into and from the receiving housing. The sensor detector can be inserted and removed, in particular screwed in and unscrewed. The closing device having its receiving housing in that way forms an adapter, which can be used to attach a sensor detector at a selected point of the partition wall contacted by the fluid to be monitored.

The closing plate of the closing device can have a sealing ring on its outer circumference. The sealing ring, in its closed position, is in sealing contact with the receiving housing or with the contact parts assigned to the receiving housing. Under the influence of the closing spring, a safe, fluid-sealed closure of the receiving opening is guaranteed when the sensor detector is removed.

In advantageous embodiments, the closing spring of the closing device is a compression spring. One end of the spring rests against the receiving housing and/or the contact parts. The other end of the spring rests on a counterholder, which is an integral part of the closing device or can be connected to the closing device.

With regard to the construction of the closing device, the arrangement can be advantageously such that the valve plate and the counterholder are held at a defined distance from each other by a web-shaped connecting piece. The connecting piece leaves fluid passages open, in particular in the direction of the counterholder. The passages, in conjunction with a further fluid passage of the counterholder, provide a fluid-conveying connection to the sensor of the sensor detector via the receiving opening released by the closing device. In this way, an installation space is provided for the compression spring along the connecting piece, while at the same time the fluid-conveying connection to the sensor is formed by the fluid passages formed on the connecting piece and on the counterholder.

In an advantageous embodiment, the counterholder has a shell part, which can be connected to the connecting piece of the valve plate and which, open to the receiving opening, forms a receptacle for the facing region of the compression spring. The counterholder has foot parts projecting from the shell part in the direction of the sensor device. Between the foot parts, fluid passages leading from the shell part to the sensor device are formed.

An annular contact part may be attached to the outer end of the receiving housing for supporting the outer end of the compression spring. The annular contact part delimits the receiving opening and forms the sealing surface for the sealing contact of the sealing ring at the valve plate of the closing device.

If the counterholder is formed having a shell part, which can be manufactured as a separate component, a snap-on connection may be provided for its connection to the connecting piece of the valve plate. The snap-on connection permits a simple assembly procedure by latching it to the connecting piece. Instead of the snap connection, a conventional bayonet lock can also be used.

Other objects, advantages and salient features of the present invention will become apparent from the following detailed description, which, taken in conjunction with the drawings, discloses preferred embodiments of the present invention.

BRIEF DESCRIPTION OF THE DRAWINGS

Referring to the drawings that form a part of this disclosure:

FIG. 1 in a side view in section, enlarged by a factor of approximately 6 compared to a practical embodiment, of a device according to a first exemplary embodiment of the invention, wherein the operating state corresponds to the functional position in which the sensor detector is placed in a partition wall, which is only partially indicated;

FIG. 2 is a side view in section of the device of FIG. 1, wherein the operating state of the inoperative functional position of the sensor device is shown;

FIG. 4 is a side view in section of a device according to a second exemplary embodiment of the invention, wherein the operating state in the functional position of the sensor device is shown; and FIG. 5 is a side view in section of the device according to the second exemplary embodiment, wherein the operating state in the inoperative functional position of the sensor detector is shown.

DETAILED DESCRIPTION OF THE INVENTION

Figure 3:
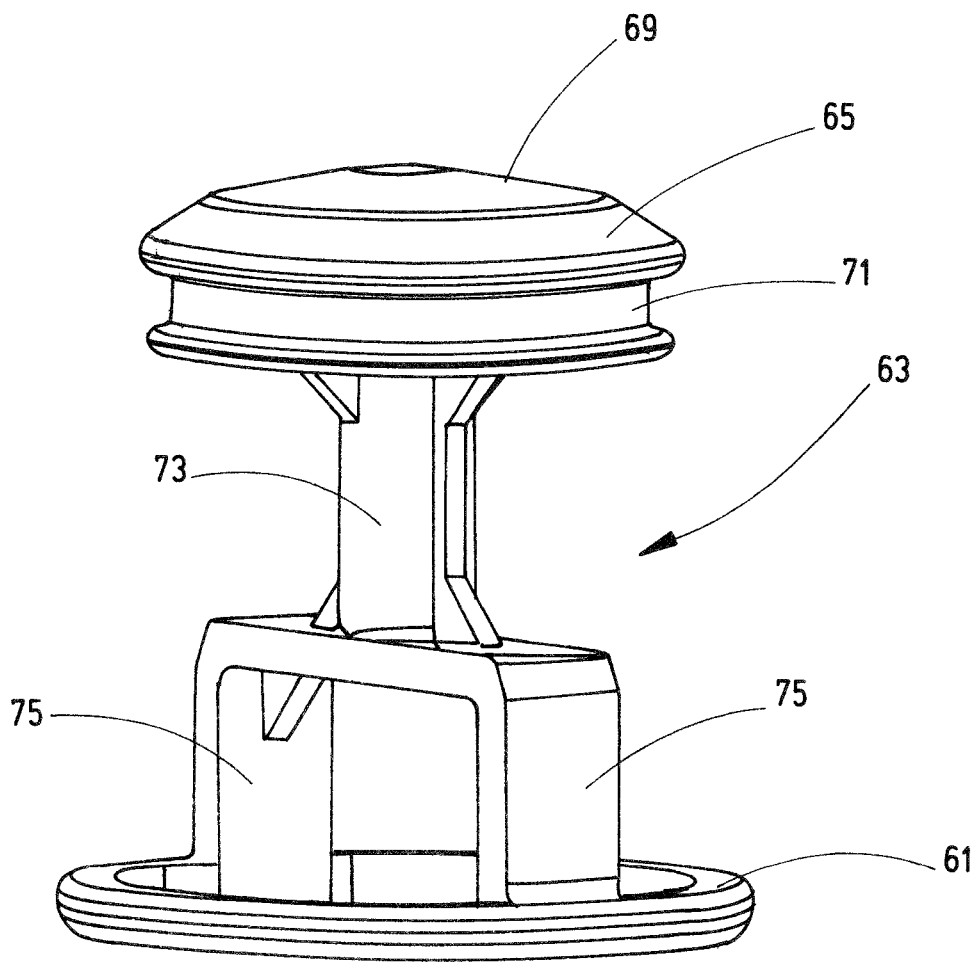
FIG. 3 is a more enlarged perspective view of the component of the first embodiment forming a closing plate and a counter holder.

FIG. 1 shows a first exemplary embodiment of the sensor device in the operating state of the functional position. The sensor device or metal particle sensor detector 1 is inserted in the associated closing device 3. A screw-in part 7, coaxial to the longitudinal axis 9 of the device, of the metal sensor housing 5 of the sensor device 1 is screwed in the threaded section of a central drilled hole 11 in a receiving housing 13 of the sensor device 1. A sealing ring 16, which is located on a step at the end of the screw-in part 7, forms the seal between the sensor housing 5 and the receiving housing 13 of the closing device 3. The receiving housing 13 of the closing device 3 is, as only indicated in FIG. 1, screwed into a threaded hole 15 in a partition wall 17. On the inside 19 of partition wall 17 the fluid to be monitored for impurities is located. For example, the partition wall 17 delimits a conduit system or a housing through which the fluid flows. A sealing ring 23 is used to seal the screwed-in receiving housing 13 with respect to the outside 21 of the partition wall 17.

Within the sensor housing 5, the sensor 25 of the sensor device 3 has a magnet carrier 27 coaxial with the longitudinal axis 9 and made of metal. The magnet carrier 27 forms a first electrode of the sensor 25. At the end face, exposed at the end of the screw-in part 7, of said magnet carrier 27, a permanent magnet 31 is held in a receptacle 29 of the magnet carrier 27. The sensor housing 5 has an internal passage that, starting from the free end of the screw-in part 7, has a first section 33 coaxial with the axis 9 and an adjoining second section 35, which extends to the open end 37 of the sensor housing 5. In this internal passage, there is an insulating body 39 in the form of an injection-molded plastic part, for example made from PA6, with which the magnet carrier 27 forming a first sensor electrode and a non-magnetic metal cylinder 41 forming a second sensor electrode are overmolded.

This metal cylinder 41 is embedded in the plastic material of the insulating body 39, coaxial with the axis 9, in such a way that it is exposed at the free end face of the screw-in part 7 and encompasses the likewise exposed end of the magnet carrier 27 forming the first electrode at a small radial distance. The lower end 43, opposite from the end face having the permanent magnet 31, of the magnet carrier 27 insulated from the sensor housing 5 is connected to a source of electrical potential, for example the positive pole of a voltage source, by a contact spring not shown. To the lower end, opposite from the upper end face, of the metal cylinder 41 forming the second electrode, a drilled hole 45 adjoins. Drilled hole 45 serves as a passage for the plastic mass. In conjunction with the sealing rings 49 and 51, a metal retaining ring 47 forms the sealed closure at the lower section 35 of the passage of the sensor housing 5. The sealing rings 49 and 51 and the ring body 47 are held by a retaining body 53 made of insulating material, for instance a thermosetting plastic. As with the magnet carrier 27 forming the first electrode, the ring body 47 is also connected to one pole of a voltage source, for example to the negative pole, as symbolically indicated in FIG. 1, via a contact spring device not shown.

The end, open to the inside 19 of the partition 17, of the drilled hole 11 in the receiving housing 13 of the closing device 3 forms the receiving opening 55 for the inlet of the fluid to be monitored. In the end area adjoining the receiving opening 55, the drilled hole 11 is drawn inwards resulting in an end rim reducing the opening diameter being formed. A shoulder surface 57 of the end rim projects radially inwards, forming a contact surface for one end of a compression spring 59. The other end of the spring 59 rests against a counterholder 61, which is located on a closing body 63 of the closing device 3. The closing body 63 is shown separately and enlarged in FIG. 3 and is arranged axially movably in the drilled hole 11 of the receiving housing 13 to form a check valve. As FIGS. 1 and 2 show, the pressure spring 59 is used to hold the counterholder 61 of the closing body 63 in contact with the front face at the end of the screw-in part 7 of the sensor housing 5. In the operating state of the device shown in FIG. 1, in which the sensor housing 5 is fully screwed into the receiving housing 13, the closing body 63 is moved into an open position against the acting spring force. In the open position, a valve plate 65 of the closing body 63 is lifted off the receiving opening 55 and moves transliterally.

FIG. 2 shows an operating condition, in which the sensor housing 5 has been already partially unscrewed from the receiving housing 13 for removal of the sensor housing 5. As a result, the closing body 63 has moved along under the effect of the compression spring 59 until the sealing ring 67, located on the outer circumference, of the valve plate 65 comes into sealing contact with the edge of the receiving opening 55 in the closed position of the valve. As FIG. 3 shows most clearly, the valve plate 65 has an annular groove 71, on the outer circumference below its slightly convex curved upper side 69, as the seat of the sealing ring 67, which is omitted in FIG. 3. A connecting piece 73 extends from the underside of the valve plate 65 as a columnar support of the valve plate 65. Webs 75 are formed on the end, opposite from the valve plate 65, of the connecting piece 73. The webs in turn form the support for the counterholder 61. The counterholder 61 has the shape of an annulus, the outside diameter of which is slightly smaller than the inside diameter of the drilled hole 11 of the receiving housing 13, so that a guide is formed for the sliding movement of the closing body 63. When the closing device 3 is open, the free spaces around the connecting piece 73 and the webs 75 form the fluid passages leading to the sensor 25 via the receiving opening 55.

FIG. 1 shows the operating condition of the functional position for the opened closing device 3. In the course of the operation of the device, when ferromagnetic dirt particles of the fluid entering via the receiving opening 55 are present, the magnetic field generated by the permanent magnet 31 at the sensor 25 results in an accumulation of particles 26 at the front end of the sensor. This accumulation results in an electrical connection between the magnet carrier 27 as the first electrode and the encompassing metal cylinder 41 as the second electrode, depending on the greater or lesser extent of the accumulation 26 and the related level of contamination of the fluid. The decrease in electrical resistance between these electrodes depends on the extent of the presence of metallic particles. When a degree of contamination exceeding a given threshold value is detected, appropriate measures are to be taken. The particle accumulation 26 has to be removed from the sensor 25. For that removal, the device is moved to the inoperative functional position by unscrewing the sensor housing 5 from the receiving housing 13. FIG. 2 shows the beginning of unscrewing process. The closing body 63 follows the axial movement of the sensor housing 5 under the influence of the compression spring 59, and the valve plate 65 reaches the blocking position closing the receiving opening 55, see FIG. 2, to permit maintenance or replacement measures, such as the removal of the accumulation 26, to be performed without fluid leakage.

The second embodiment shown in FIGS. 4 and 5 differs from the first embodiment mainly by a modified construction of the closing device 3. The sensor housing 5 comprising its associated components is unchanged in comparison to the first example. In contrast to the first embodiment, where the closing body 63 is formed as a one-piece injection molded component made of a plastic material, such as PA6, for instance with glass fiber reinforcement, or made of a metal material, the closing body 63 in the second embodiment is formed bi-partite from such materials. Instead of the counterholder 61, which in the first embodiment is formed directly on the webs 75 of the connecting piece 73, in the second embodiment the counterholder is formed by a shell part 77. Shell part 77 is attached by a snap connection to the connecting piece 73 of the closing body 63, which extends in the form of a cylindrical spigot from the valve plate 65. The shell part 77 has the shape of a round shell open in the direction of the valve plate 65. The side wall 79 of the shell part 77 is guided axially movable in the drilled hole 11 of the receiving housing 13. A sleeve part 81 extends away from the central area of the shell bottom, surrounds the lower length section of the connecting piece 73 and forms the snap-on connection with inwardly projecting nubs 83, which can be latched to notches in the connecting piece 73. In addition to passages 85 in the bottom of the shell part 77, foot parts 87 extend downwards, which are held in contact with the end face of the sensor 25 at the end of the screw-in part 7 of the sensor housing 5 under the action of the compression spring 59, which rests on the bottom of the shell part 77 as the counterholder. In contrast to the first embodiment, where the contact part for the upper end of the compression spring 59 is formed by a shoulder surface 57 on the receiving housing 13, the present second embodiment is provided with a separate contact part in the form of a annulus 89, which delimits the receiving opening 55 and is attached to the free end edge 91 of the receiving housing 13 by caulking. The annulus 89 forms the sealing surface which, in the closed position of the formed check valve, interacts with the sealing ring 67 on the valve plate 65.

The mode of operation of the second embodiment is equal to that of the first embodiment. As in the first example, where the fluid path from the open receiving opening 55 to the front side of the sensor 25 is routed via the free spaces formed between the webs 75 on the connecting piece 73 of the closing body 63, in the second embodiment a fluid path is formed from the inside of the shell part 77 via the passages 85, formed in the shell bottom, between the base parts 87. For use with fluids at a corresponding pressure level, for example in the range of 10 to 30 bar, preferably 16 bar, the entire housing formed by the screwed together housing parts, the sensor housing 5 and the receiving housing 13, is pressure-resistant and can be made pressure-sealed by the sealing elements 16, 23, 49 and 51. Stainless steel or zinc coated steel are advantageous housing materials.

While various embodiments have been chosen to illustrate the invention, it will be understood by those skilled in the art that various changes and modifications can be made therein without departing from the scope of the invention as defined in the claims.

The invention claimed is:

1. A sensor device for detecting metal particles contaminating a fluid flowing through a fluid passage delimited by a partition wall with a hole extending through the partition wall, the sensor device comprising:
   a sensor detector capable of detecting metal particles in the fluid passage removably mountable in the hole by a receiving housing, at least partially encompassable by the partition wall and movable between an inoperative position removed from the partition wall and a functional position connected in fluid communication with the fluid passage; and
   a closing device interacting with the sensor detector to close a receiving opening in the receiving housing blocking fluid communication with the fluid passage when the sensor detector is in the inoperative position and to open the receiving opening providing fluid communication with the fluid passage when the sensor detector is moved to the functional position, the closing device including a closing plate being biased by a compression spring toward a closed position closing the receiving opening and being movable to an open position opening the receiving opening against biasing of the compression spring by movement of the sensor detector to the functional position relative to the closing plate, a first end the compression spring engaging the receiving housing, a second end of the compression spring engaging a counterholder, the counterholder being an integral part of or being connected to the closing plate, the closing plate and the counterholder being spaced from one another by a web-shaped connecting piece with open fluid passages, the open fluid passages of the connecting piece and fluid passages in the counterholder providing a fluid communication connection to the sensor detector via the receiving opening when the closing plate is on the open position by engagement of the sensor detector with the counterholder.

2. A sensor device according to claim 1 wherein the closing plate has a sealing ring on an outer circumference thereof in sealing contact the receiving housing in the closed position thereof.

3. A sensor device according to claim 1 wherein the receiving housing comprises an annular contact part on an outer end of the receiving housing delimiting the receiving opening and forming a sealing surface abutting a sealing ring an outer circumference of the closing plate, the first end of the compression spring engaging the annular contact part.

4. A sensor device according to claim 1 wherein the sensor detector is in the receiving housing in the functional position thereof; and the closing plate is outside the receiving housing in the open position thereof.

5. A sensor device according to claim 1 wherein the counterholder comprises a shell part being connected to the connecting piece forming a receptacle receiving the second end of the compression spring, being open to the receiving opening and having foot parts projecting from the shell part in a direction of the sensor detector with fluid passages being between the foot parts leading from the shell part to the sensor detector.

6. A sensor device according to claim 5 wherein the shell part is latched to the connecting piece by a snap-on connection.

7. A sensor device according to claim 1 wherein the receiving opening is delimited by the receiving housing inserted in the hole in the partition wall, and permanently receives the closing device therein, the sensor detector being insertable in and removable from the receiving housing.

8. A sensor device according to claim 7 wherein the sensor detector is threadedly engaged with the receiving housing.

9. A sensor device according to claim 7 wherein the receiving housing is threadedly engaged in the hole in the partition wall. with fluid passages being between the foot parts leading from the shell part to the sensor detector.

10. A sensor device according to claim 9 wherein the closing plate is movable translaterally along a longitudinal axis of the receiving housing.

* * * * *